United States Patent
Estrela Ariquel et al.

(10) Patent No.: US 8,227,510 B2
(45) Date of Patent: Jul. 24, 2012

(54) COMBINE USE OF PTEROSTILBENE AND QUERCETIN FOR THE PRODUCTION OF CANCER TREATMENT MEDICAMENTS

(75) Inventors: José María Estrela Ariquel, Valencia (ES); Gregorio Asensio Aguilar, Valencia (ES); Miguel Angel Asensi Miralles, Valencia (ES); Elena Obrador Plá, Valencia (ES); Maria Teresa Varea Muñoz, Valencia (ES); Leonardo Jordá Quilis, Valencia (ES); Paula Ferrer Pastor, Valencia (ES); Ramón Segarra Guerrero, Valencia (ES); Angel Ortega Valero, Valencia (ES); Maria Benlloch Garcia, Valencia (ES)

(73) Assignee: Universitat de Valencia, Valencia (ES)

( * ) Notice: Subject to any disclaimer, the term of this patent is extended or adjusted under 35 U.S.C. 154(b) by 1084 days.

(21) Appl. No.: 11/631,912

(22) PCT Filed: Jul. 19, 2005

(86) PCT No.: PCT/ES2005/070104
§ 371 (c)(1),
(2), (4) Date: Jun. 5, 2008

(87) PCT Pub. No.: WO2006/024685
PCT Pub. Date: Mar. 9, 2006

(65) Prior Publication Data
US 2011/0224290 A1    Sep. 15, 2011

(30) Foreign Application Priority Data
Jul. 20, 2004   (ES) .................................. 200401846

(51) Int. Cl.
*A61K 31/35* (2006.01)
(52) U.S. Cl. ...................................................... 514/456
(58) Field of Classification Search .................. 514/456
See application file for complete search history.

(56) References Cited

U.S. PATENT DOCUMENTS

| | | | | |
|---|---|---|---|---|
| 5,770,593 | A | * | 6/1998 | Grunicke et al. ............. 514/200 |
| 5,977,184 | A | * | 11/1999 | Birdsall et al. ................ 514/685 |
| 6,245,814 | B1 | * | 6/2001 | Nag et al. ...................... 514/570 |
| 6,680,342 | B2 | | 1/2004 | Young et al. |

OTHER PUBLICATIONS

Ortega et al, Mar. 1, 2004, American Association for Cancer Research Meeting Abstracts, 883-b.*
Rimando et al, J Nat Prod, 1994, 4, 267-272.*
Ferrer, P., et al "Association between Pterostilbene and Quercetin Inhibits Metastatic Activity of B16 Melanoma" *Neoplasia* (2005) vol. 7, No. 1 pp. 37-47.
Rimando A.M., et al "Cancer Chemopreventive and Antioxidant Activities of Pterostilbene, a Naturally Occurring Analogue of Resveratrol" *J. Agric. Food Chem* (2002) vol. 50, pp. 3453-3457.
Paul B. Masih, et al "Occurrence of resveratrol and pterostilbene in age-old darakchasava, an ayurvedic medicine from India" *J. Ethnopharmacol* (1999), vol. 68, No. 1-3, 71-6.

* cited by examiner

*Primary Examiner* — Jeffrey S. Lundgren
*Assistant Examiner* — Ibrahim D Bori
(74) *Attorney, Agent, or Firm* — Ladas & Parry LLP

(57) ABSTRACT

The invention relates to the combined use of pterostilbene and quercetin for the production of cancer treatment medicaments. The in vitro growth of melanoma cells B16-F10 (B16M-F10) is inhibited (56%) by combined exposures of short duration (60 min/day) to PTER (40 μM)+QUER(20 μM) (~average values of plasma concentrations measured within the first hour following the IV administration of 20 mg of each polyphenol/kg ~). The combined intravenous administration of PTER+QUER (20 mg/kg× day) to mice inhibits (73%) the metastatic growth of melanoma B16M-F10 in the liver, a common site for metastasis development. The invention demonstrates that the combination of PTER+QUER inhibits the growth of malignant melanoma metastasis and prolongs the survival of the carrier host.

3 Claims, 2 Drawing Sheets

COMBINE USE OF PTEROSTILBENE AND QUERCETIN FOR THE PRODUCTION OF CANCER TREATMENT MEDICAMENTS

FIELD OF THE INVENTION

The invention relates to the pharmaceutical field, concretely to the combined use of 2 active principles, pterostilbene and quercetin, in the manufacture of medicinal products that can be used for cancer treatment.

STATE OF THE ART

Various phenolic compounds, including resveratrol (RESV), display powerful antioxidant effects and may have therapeutic applications in diseases related to oxidative stress such as cancer (1-3). The anticancer activity of RESV was reported for the first time by Jang et al. in 1997 (4). The mechanisms by which RESV exerts its antitumor effects are being actively investigated (3) and may include for example: a) inhibition of ribonucleotide reductase (5), DNA polymerase (6), protein kinase C (7), or cyclooxygenase-2 (8) activities; b) inhibition of carcinogenesis mediated by reactive species of oxygen (4) or of cellular proliferation (9); and c) activation of cell death by apoptosis (10-13). However, the RESV-mediated potential inhibition of cancer growth is severely limited owing to its low bioavailability (14). Consequently, it appears that structural changes are necessary in the RESV molecule in order to increase its bioavailability while preserving its biological activity. The OH of 4' and the stereoisomerism in its trans conformation are absolutely necessary for inhibition of cellular proliferation (15). Pterostilbene (PTER), a naturally occurring analog, of RESV but approximately 60-100 times more powerful as an antifungal agent, exhibits similar anticancer properties (16). Furthermore, the flavonoids are some of the most powerful antioxidants because they have one or more of the following structural elements: an o-diphenolic group, a double bond at 2-3 conjugated with the 4-oxo function, OH groups in positions 3 and 5. Quercetin (QUER) combines these three properties, and previous studies have confirmed that it also has antitumor properties, probably due to immune stimulation, elimination of free radicals, alteration of the mitotic cycle of the tumor cells, modification of gene expression, antiangiogenic activity, or induction of apoptosis, or a combination of these effects (2, 17). Concretely, QUER has been described (US 2003/0054357) in the treatment of prostate cancer. There are patents (WO02/34262) which highlight the antioxidant effect of certain flavonoids, concretely of a combination of quercetin plus catechin for use in the treatment and prevention of circulatory or cardiac disorders, by preventing platelet aggregation.

However, since it has not been demonstrated that the potential anticancer effects are effective in systemic administration, we investigated the anticancer properties of combined systemic administration of PTER and QUER at bioavailable concentrations. We found that their combination strongly inhibits the growth of the metastatic malignant melanoma B16-F10 (B16M-F10).

ABBREVIATIONS

B16M-F10, melanoma B16-F10; RESV, resveratrol; t-RESV, trans-resveratrol; PTER, pterostilbene; t-PTER, trans-pterostilbene; QUER, quercetin; HSE, hepatic sinusoidal endothelium; VCAM-1, vascular cell adhesion molecule 1; VLA-4, very late activation antigen 4; B16M-F10/Tet-Bcl-2, melanoma B16-F10 that overexpresses Bcl-2; LC-MS/MS, high-performance liquid chromatography and mass spectrometry; i.v., intravenous/intravenously; i.p., intraperitoneal; SD, standard deviation.

REFERENCES

[1] Yang C S, Landau J M, Huang M T, and Newmark H L (2001). Inhibition of carcinogenesis by dietary polyphenolic compounds. *Annu Rev Nutr* 21, 381-406.

[2] Ross J A, and Kasum C M (2002). Dietary flavonoids: bioavailability, metabolic effects, and safety. *Annu Rev Nutr* 22, 19-34.

[3] Pervaiz S (2003). Resveratrol: from grapevines to mammalian biology. *FASEB J* 17, 1975-1985.

[4] Jang M, Cai L, Udeani G O, Slowing K V, Thomas C F, Beecher C W, Fong H H, Farnsworth N R, Kinghorn A D, Mehta R G, et al. (1997). Cancer chemopreventive activity of resveratrol, a natural product derived from grapes. *Science* 275, 218-220.

[5] Fontecave M, Lepoivre M, Elleingand E, Gerez C, and Guittet O (1998). Resveratrol, a remarkable inhibitor of ribonucleotide reductase. *FEBS Lett* 421, 277-279.

[6] Sun N J, Woo S H, Cassady J M, and Snapka R M (2003). DNA polymerase and topoisomerase II inhibitors from Psoralea corylifolia. *J Nat Prod* 66, 734.

[7] Stewart J R, Ward N E, Ioannides C G, and O'Brian C A (1999). Resveratrol preferentially inhibits protein kinase C-catalyzed phosphorylation of a cofactor-independent, arginine-rich protein substrate by a novel mechanism. *Biochemistry* 38, 13244-13251.

[8] Subbaramaiah K, Chung W J, Michaluart P, Telang N, Tanabe T, Inoue H, Jang M, Pezzuto J M, and Dannenberg A J (1998). Resveratrol inhibits cyclooxygenase-2 transcription and activity in phorbol ester-treated human mammary epithelial cells. *J Biol Chem* 273, 21875-21882.

[9] Sauer H, Wartenberg M, and Hescheler J (2001). Reactive oxygen species as intracellular messengers during cell growth and differentiation. *Cell Physiol Biochem* 11, 173-186.

[10] Clement M V, Hirpara J L, Chawdhury S H, and Pervaiz S (1998). Chemopreventive agent resveratrol, a natural product derived from grapes, triggers CD95 signaling-dependent apoptosis in human tumor cells. *Blood* 92, 996-1002.

[11] She Q B, Bode A M, Ma W Y, Chen N Y, and Dong Z (2001). Resveratrol-induced activation of p53 and apoptosis is mediated by extracellular-signal-regulated protein kinases and p38 kinase. *Cancer Res* 61, 1604-1610.

[12] Tinhofer I, Bernhard D, Senfter M, Anether G, Loeffler M, Kroemer G, Kofler R, Csordas A, and Greil R (2001). Resveratrol, a tumor-suppressive compound from grapes, induces apoptosis via a novel mitochondrial pathway controlled by Bcl-2. *FASEB J* 15, 1613-1615.

[13] Scarlatti F, Sala G, Somenzi G, Signorelli P, Sacchi N, and Ghidoni R (2003). Resveratrol induces growth inhibition and apoptosis in metastatic breast cancer cells via de novo ceramide signaling. *FASEB J* 17, 2339-2341.

[14] Asensi M, Medina I, Ortega A, Carretero J, Bano M C, Obrador E, and Estrela J M (2002). Inhibition of cancer growth by resveratrol is related to its low bioavailability. *Free Radic Biol Med* 33, 387-398.

[15] Stivala L A, Savio M, Carafoli F, Perucca P, Bianchi L, Maga G, Forti L, Pagnoni U M, Albini A, Prosperi E, et al. (2001). Specific structural determinants are responsibie for the antioxidant activity and the cell cycle effects of resveratrol. *J Biol Chem* 276, 22586-22594.

[16] Rimando A M, Cuendet M, Desmarchelier C, Mehta R G, Pezzuto J M, and Duke S O (2002). Cancer chemopreventive and antioxidant activities of pterostilbene, a naturally occurring analogue of resveratrol. *J Agric Food Chem* 50, 3453-3457.

[17] Lamson D W, and Brignall M S (2000). Antioxidants and cancer, part 3: quercetin. *Altern Med Rev* 5, 196-208.

[18] Tuck K L, Tan H W, and Hayball P J (2000). A simple procedure for the deuteration of phenols. *Journal of Labelled Compounds and Radiopharmaceuticals* 43, 817-823.

[19] Navarro J, Obrador E, Pellicer J A, Aseni M, Vina J, and Estrela J M (1997). Blood glutathione as an index of radiation-induced oxidative stress in mice and humans. *Free Radic Biol Med* 22, 1203-1209.

[20] Carretero J, Obrador E, Esteve J M, Ortega A, Pellicer J A, Sempere F V, and Estrela J M (2001). Tumoricidal activity of endothelial cells. Inhibition of endothelial nitric oxide production abrogates tumor cytotoxicity induced by hepatic sinusoidal endothelium in response to B16 melanoma adhesion in vitro. *J Biol Chem* 276, 25775-25782.

[21] Anasagasti M J, Martin J J, Mendoza L, Obrador E, Estrela J M, McCuskey R S, and Vidal-Vanaclocha F (1998). Glutathione protects metastatic melanoma cells against oxidative stress in the murine hepatic microvasculature. *Hepatology* 27, 1249-1256.

[22] Carretero J, Obrador E, Anasagasti M J, Martin J J, Vidal-Vanaclocha F, and Estrela J M (1999). Growth-associated changes in glutathione content correlate with liver metastatic activity of B16 melanoma cells. *Clin Exp Metastasis* 17, 567-574.

[23] Ohigashi H, Shinkai K, Mukai M, Ishikawa O, Imaoka S, Iwanaga T, and Akedo H (1989). In vitro invasion of endothelial cell monolayer by rat ascites hepatoma cells. *Jpn J Cancer Res* 80, 818-821.

[24] Braman R S, and Hendrix S A (1989). Nanogram nitrite and nitrate determination in environmental and biological materials by vanadium (III) reduction with chemiluminescence detection. *Anal Chem* 61, 2715-2718.

[25] Okahara H, Yagita H, Miyake K, and Okumura K (1994). Involvement of very late activation antigen 4 (VLA-4) and vascular cell adhesion molecule (VCAM-1) in tumor necrosis factor alpha enhancement of experimental metastasis. *Cancer Res* 54, 3233-3236.

[26] Obrador E, Carretero J, Esteve J M, Pellicer. J A, Pascual A, Petschen I, and Estrela J M (2001). Glutamine potentiates TNF-alpha-induced tumor cytotoxicity. *Free Radic Biol Med* 31, 642-650.

[27] Eissa S, and Seada L S (1998). Quantitation of bcl-2 protein in bladder cancer tissue by enzyme immunoassay: comparison with Western blot and immunohistochemistry. *Clin Chem* 44, 1423-1429.

[28] Rimm E B, Katan M B, Ascherio A, Stampfer M J, and Willett W C (1996). Relation between intake of flavonoids and risk for coronary heart disease in male health professionals. *Ann Intern Med* 125, 384-389.

[29] Day A J, Bao Y, Morgan M R, and Williamson G (2000). Conjugation position of quercetin glucuronides and effect on biological activity. *Free Radic Biol Med* 29, 1234-1243.

[30] Goldberg D M, Van J, and Soleas G J (2003). Absorption of three wine-related polyphenols in three different matrices by healthy subjects. *Clin Biochem* 36, 79-87.

[31] Off F W, Wang H R, Lafrenie R M, Scherbarth S, and Nance D M (2000). Interactions between cancer cells and the endothelium in metastasis. *J Pathol* 190, 310-329.

[32] Burdon R H (1995). Superoxide and hydrogen peroxide in relation to mammalian cell proliferation. *Free Radic Biol Med* 18, 775-794.

[33] Fremont L (2000). Biological effects of resveratrol. *Life Sci* 66, 663-673.

[34] Bravo L (1998). Polyphenols: chemistry, dietary sources, metabolism, and nutritional significance. *Nutr Rev* 56, 317-333.

[35] Walle T (2004). Absorption and metabolism of flavonoids. *Free Radic Biol Med* 36, 829-837.

[36] Davies K J (1995). Oxidative stress: the paradox of aerobic life. *Biochem Soc Symp* 61, 1-31.

DESCRIPTION OF THE INVENTION

For the purposes of the invention, PTER and QUER are also to be understood as meaning any pharmaceutically acceptable salt, particularly the sulfates of both polyphenols, as well as any other pharmaceutically acceptable derivative, particularly the glucuronides of any of the above-mentioned polyphenols.

The bioavailability and the biological efficacy in vivo are critical factors that have to be correlated before drawing any conclusion about the potential health benefits of the polyphenols (14, 30, 33, 34). As shown in FIG. 2, where the effect of t-RESV, t-PTER, or QUER was studied, inhibition of the proliferation of B16M-F10 cells in vitro was more potent in the presence of t-PTER+QUER. The bioavailable concentrations of PTER and QUER, measured in the plasma after oral administration, were unable to inhibit the growth of B16M-F10 cells, even in cases when the concentrations of these polyphenols were constant throughout the culture time, see Example 2. However, the bioavailable concentrations of PTER or QUER, measured in the plasma after i.v. administration (see FIG. 1), inhibited tumor growth by up to 56%, even in cases when both polyphenols were only present for 60 minutes in each 24 hours of culture (FIG. 2), without increasing the rate of cell death (cell viability still being>95%, as in the controls, in all cases).

On the basis of these facts, concerning the differences in bioavailability, and the data shown in FIG. 2, we selected the combination PTER+QUER for studying its effect on metastatic progression. As shown in Table 3, the effect of t-PTER, QUER, t-RESV, or combinations thereof, on the in-vitro interaction between B16M-F10 cells and the vascular endothelium was investigated. Parallel with the effect on tumor growth (FIG. 2), the combination of PTER plus QUER was the one that displayed the greatest capacity for reducing (by approximately 74%) the formation of tumor colonies in an in-vitro invasion test (Table 3).

To demonstrate that natural polyphenols such as t-PTER and QUER inhibit the metastatic growth in vivo of a highly malignant tumor and increase the survival of the carrier, we employed daily i.v. administration of high doses (20 mg/kg of body weight administered once daily). However, various possible protocols can be considered at this point. For example, if it proved more effective, and nontoxic to humans, the doses could be increased. Furthermore, our results do not rule out possible benefits from the use of oral administration.

In fact, t-RESV inhibits the expression of VCAM-1 at very low concentrations (1 μM) (14). Nevertheless, as pointed out by Goldberg et al. (30) and taking into account the metabolism in vivo of these small polyphenols (see for example 34-35), investigations of this nature ought to focus on the benefits of its conjugates (for example glucuronides and sulfates). Moreover, the doses required for inhibiting metastatic growth may depend on the type of cell. Furthermore, the combination t-PTER+QUER might also be useful in other pathologies associated with oxidative stress (for example diabetes, arteriosclerosis, neurodegenerative diseases, or ischaemic heart disease) (36) where the doses required for obtaining benefits might be similar or completely different. In conclusion, our findings highlight the applications of combinations of polyphenols in cancer therapy. Moreover, since the administration of polyphenols can be combined with biotherapy, cytotoxic drugs and/or ionizing radiation, the mechanisms described in the invention may have useful applications for improving therapy against metastatic melanoma and, possibly, against other types of malignant tumors.

DETAILED DESCRIPTION OF THE INVENTION

Example 1

Plasma Levels of Pterostilbene and Quercetin Animals and "in-vivo" Administration of Polyphenols The mice (C57BL/6J, male, 6-8 weeks) were from Charles River Spain (Barcelona). The procedures and animal care were based on institutional standards and complied with national and international laws and policies (Directive 86/609, OJ L 358. 1 of the Council of the European Community, of 12 Dec. 1987) and the "Guide for the Care and Use of Laboratory Animals" of the National Institutes of Health (NIH, USA) (NIH Publication No. 85-23, 1985). All the animals were fed according to concentrated laboratory diets (Letica, Barcelona, Spain) allowing them free access to food and submitting them to a cycle of 12 hours of light/12 hours of darkness with ambient temperature of 22° C. The experiments were begun at 10.00 a.m. to minimize the effects of diurnal variations.

For the pharmacokinetic studies and for the daily treatment, the mice were administered i.v. (via the jugular vein, where a permanent catheter had previously been fixed by surgical methods; i.v. administration was carried out slowly for 1 minute), and orally (via stomach tube), 20 mg/kg of t-PTER (dissolved in ethanol 0.5 ml/kg of animal weight) or QUER (dissolved in dimethylsulfoxide:saline, 1:0.5 0.15 ml/kg of weight). In general, the compositions based on a combination of PTER and QUER can contain, as excipients, those stated previously or any others that are pharmaceutically acceptable. The presentation of said compositions can be, non-limitatively, in the form of solids such as tablets, capsules, pellets, pills, etc. and liquid presentations such as drops, syrups, injectables, etc. Moreover, the active principles (PTER and QUER) of the composition can be in their uncombined forms or in the form of pharmaceutically acceptable salts, including esters. The t-PTER was synthesized in our laboratory following standardized reactions of Wittig and Heck (www.orgsyn.org), whereas the QUER was obtained from Sigma Chemical Co. (San Luis, Mo., USA). The $^3$H-t-PTER (2.2 Ci/mmol), labeled in the ortho and para positions of the benzene rings, was prepared in our laboratory according to a method similar to that used for the deuteration of phenols (18). $^{14}$C-QUER (50 mCi/mmol), labeled in position 4 of the carbon ring, was obtained from the NCI Radiochemical Carcinogen Repository of Chemsyn Laboratories (Kansas City, Mo., USA). The radioactivity was measured using a Varisette 2700 TR analyzer from Packard. Blood was collected by means of the catheter in 1-ml syringes that contained heparin sodium (0.05 ml of a 5% solution in 6.9% NaCl). The plasma and the erythrocytes were separated as described previously (19).

Determination of Pterostilbene and Quercetin by Liquid Chromatography and Mass Spectrometry (LC-MS/MS)

LC-MS/MS was carried out using a Quattro Micro triple quadrupole mass spectrometer (Micromass, Manchester, UK) equipped with an LC-10Advp pump, an SLC-10Avp control system and an SIL-10Advp autoinjector from Shimadzu. The samples were analyzed by reverse-phase high-performance liquid chromatography using a Prodigy ODS column (100×2 mm) from Phenomenex (Torrance, Calif., USA), with a particle size of 3 µm. In all cases, 40 µl was injected into the column. Column temperature was maintained at 25° C. The following gradient system was used, pumped through the column at 0.2 ml/minute (min/% A/% B/% C) (A, methanol; B, 10% acetonitrile and 90% ammonium formate 10 mM pH 3.75; C, ammonium formate 10 mM pH 3.75): 0/5/5/90, 10/5/5/90, 20/5/90/5, 30/100/0/0, 40/5/5/90. The negative ion tandem mass spectra obtained by electrospray were recorded with the electrospray capillary fixed at 3.5 keV and at a temperature of the source block of 120° C. Nitrogen was used as nebulizer gas and drying gas, with flows of 300 and 30 l/h, respectively. Argon at $1.5 \times 10^{-3}$ mbar was used as the collision gas for collision-induced dissociation. A test was carried out based on LC-MS/MS with tracking of multiple reactions using the transitions m/z 255-240 for PTER and 300-151 for QUER, which in both cases represent favorable fragmentation routes for these deprotonated molecules. The calibration curves were obtained using a reference standard of PTER or QUER (0.01-100 µM) and it was found in each case that they were linear with coefficients of correlation>0.99. The limits of detection and quantification of our method were 0.01 µM.

Depending on dietary habits, the human intake of flavones and flavonols (the commonest flavonoids) is ~3-70 mg/day, of which between 60 and 70% is QUER [the main sources include tea, wine, berries, apples and onions (28)]. However, there are no reports on estimates for the intake of PTER, which is present for example in extracts from the duramen of *P. marsupium*, and is employed in ayurvedic medicine for the treatment of diabetes, and in black grapes (although quantitative studies have shown that for every 10 parts of RESV, there are only 1-2 parts of PTER) (16 and references therein). As shown in FIG. 1, after i.v. administration of 20 mg/kg of t-PTER or QUER to mice (a dose which represents, for a human adult with 70 kg body weight, ~1000 times the maximum amount of PTER found in one kilogram of black grapes, and ~20 times the maximum daily intake of QUER), their highest plasma concentrations (~95 µM of PTER and ~46 µM of QUER 5 minutes after administration) decreases to ~1 µM in 120 minutes for QUER and 480 minutes for PTER. Following an identical protocol, previously we found that the highest concentration of QUER in plasma ~43 µM (5 minutes after i.v. administration to rabbits) falls to ~1 µM in 60 minutes (14). We calculated a plasma half-life of RESV in the mouse of ~10.2 minutes (Estrela et al., unpublished data). From the data in FIG. 1, we calculated a half-life of PTER and QUER of ~77.9 and 20.1 minutes, respectively (see FIG. 1). The levels of PTER and QUER in whole blood of mice were not significantly different from those mentioned previously for the plasma. At least 99% of the PTER measured in plasma or blood was in the trans form.

For comparison, t-PTER or QUER (20 mg/kg) was also administered orally. A mixture of $^3$H-t-PTER (5 µCi/mouse) and t-PTER without labeling or of $^{14}$C-QUER (2 µCi/mouse) and QUER without labeling was administered, for the purpose of differentiating between unchanged free polyphenols and their metabolites/conjugates generated in vivo. In order to calculate the free forms, we effected measurements by LC/MS-MS (see the methodology described previously in this document). After applying the corresponding corrections per dilutions, the radioactivity of the samples that contained only free PTER or QUER was subtracted from the total radioactivity measured in an equivalent sample of plasma. As shown in Table 1, after oral administration the plasma levels of PTER and QUER showed some peaks at 60 and 10 minutes, respectively. However, the total levels of PTER and QUER (unchanged free polyphenols plus their metabolites and conjugated forms) were very different. The total concentration of PTER was >10 µM between 30 and 240 minutes after its administration, whereas the levels of total QUER only remained >1 µM in the first 10 minutes (Table 1). During these periods of time, the free PTER represented a small percentage of the total (15-35%), whereas free QUER (except for the first 5 minutes) was almost undetectable (0.5%) (Table 1).

TABLE 1

Plasma levels of pterostilbene and quercetin after oral administration in mice.

| Time (minutes) | PTER (µM) | PTER (% free) | QUER (µM) | QUER (% free) |
|---|---|---|---|---|
| 5 | 2.9 ± 0.6 | 67 ± 13 | 1.6 ± 0.3 | 22 ± 6 |
| 10 | 6.6 ± 1.8* | 50 ± 10 | 2.3 ± 0.7 | <0.5* |
| 30 | 11.1 ± 3.0* | 35 ± 5* | 0.6 ± 0.2* | <0.5* |
| 60 | 18.2 ± 2.7* | 17 ± 6* | 0.2 ± 0.1* | <0.5* |
| 120 | 13.3 ± 3.4* | 15 ± 3* | 0.07 ± 0.01* | <0.5* |
| 240 | 10.6 ± 1.2* | 16 ± 4* | 0.05 ± 0.02* | <0.5* |
| 480 | 7.1 ± 0.8* | 14 ± 4* | 0.05 ± 0.02* | <0.5* |
| 720 | 1.6 ± 0.5* | 12 ± 2* | 0.04 ± 0.01* | <0.5* |
| 1440 | n.d. | n.d. | n.d. | n.d. |

The animals were treated with 20 mg/kg of body weight of t-PTER or QUER. A group of 6-7 mice was sacrificed at each time point. Not detectable=n.d. *$P<0.01$ comparing the data obtained at 10-1440 minutes with the data found 5 minutes after administration of the polyphenol.

Extravascular Levels of Pterostilbene and Quercetin

To supplement the pharmacokinetics in plasma/blood, we also evaluated the bioavailability of PTER and QUER in extravascular tissues. As shown in Table 2, after their i.v. administration to mice, the highest content of PTER and QUER in brain, lung, liver and kidney occurred within the first 5 minutes after administration (Table 2). Therefore, it appears that neither of the polyphenols is subject to extravascular accumulation and that their presence in various tissues (Table 2) is parallel in time to their bioavailability in the bloodstream (FIG. 1).

10-60 minutes with the data found 5 minutes after administration of the polyphenol.

Example 2

Inhibition of the Growth of Melanoma B16 Cells "in vitro"

Culture of Tumor Cells

B16M-F10 cells were cultured in Dulbecco's modified Eagle's medium (DMEM; Gibco Labs., Grand Island, N.Y., USA), pH 7.4, supplemented with 10% fetal serum (Gibco), HEPES 10 mM, $NaHCO_3$ 40 mM, 100 U/ml of penicillin and 100 µg/ml of streptomycin (20).

The B16M-F10 melanoma, highly aggressive, is a model that is widely used for investigating metastatic spread and tissue invasion (21), and for this reason was chosen for our studies. In the first group of experiments, we studied the effect in vitro of t-PTER+QUER on the growth of B16M-F10 cells. To reproduce the conditions in vivo after i.v. administration, we incubated B16M-F10 cells in the presence of t-PTER (40 µM) and/or QUER (20 µM) for a limited period (60 minutes) (this represents a value that approximates to the average of the concentrations of PTER and QUER measured in the plasma during the first hour after i.v. administration of 20 mg/kg of each polyphenol (FIG. 2). For comparison, we also used t-RESV (12 µM; selection of this concentration was based on a similar criterion, see the data cited in ref. 14). The polyphenols were added to the incubation medium every 24 hours and, as mentioned, they were only present for 60 minutes. As shown in FIG. 2, t-PTER and QUER inhibited the growth of B16M-F10 by 40 and 19%, respectively. However, when both were present the inhibition of growth increased to ~56%, which suggests an additive effect (in the presence of t-PTER+QUER ~77.7% of the cells accumulated in G0/G1, whereas ~13.2% and 9.1% were in phases S and G2/M, respectively; moreover, the controls, which were growing exponentially, displayed a distribution of the cell cycle of ~58.0% in G0/G1, 22.4% in S and 19.6% in G2/M; n=6 in both cases; cell viability was still >95% in all cases). In our experimental conditions, t-RESV did not have a significant effect on the growth rate of tumor cells (FIG. 2). Furthermore, t-RESV did not significantly affect the percentage inhibition of the growth of B16M-F10 promoted by t-PTER+QUER (FIG. 2).

Also for comparison, we incubated B16M-F10 cells in the presence of t-PTER+QUER at concentrations representing an approximate average value of the total level of each polyphenol measured in the plasma in the first hour after oral administration (11 µM of PTER and 1 µM of QUER) (see Table 1).

TABLE 2

Extravascular levels of pterostilbene and quercetin after intravenous administration in mice.

| Time (min) | Brain | | Lung | | Liver | | Kidney | |
|---|---|---|---|---|---|---|---|---|
| | PTER | QUER | PTER | QUER | PTER | QUER | PTER | QUER |
| 5 | 5 ± 1 | 4 ± 1 | 36 ± 6 | 15 ± 3 | 14 ± 4 | 9 ± 3 | 3 ± 1 | 1 ± 0.2 |
| 10 | 2 ± 0.5* | 2 ± 0.4* | 15 ± 3* | 8 ± 2* | 7 ± 1* | 3 ± 1* | 3 ± 0.3 | 1 ± 0.5 |
| 30 | n.d. | n.d. | 6 ± 1* | 2 ± 0.6* | 3 ± 0.5* | 1 ± 0.2* | 2 ± 0.4* | n.d. |
| 60 | n.d. | n.d. | 2 ± 1* | n.d. | n.d. | n.d. | 1 ± 0.3* | n.d. |

The animals were treated with t-PTER or QUER (20 mg/kg, containing 5 µCi of $^3$H-t-PTER or 2 µCi $^{14}$C-QUER). A group of 4-5 mice was sacrificed at each time point. Not detectable=n.d. *$P<0.01$ comparing the data obtained at Both polyphenols, as free forms, were constantly present in the incubation medium. Although both PTER and QUER undergo metabolic transformations after oral administration, the use of free forms is a valid approach since it is not to be expected that their metabolites/conjugates would display more potent antitumor activity (see for example refs. 29-30). However, in these conditions t-PTER (11 μM) and/or QUER (1 μM) did not have a significant effect on the levels of control of growth of the B16M-F10 cells in vitro (similar levels of control corresponding to those in FIG. 2).

The total levels of free polyphenols added to the incubation medium remained unchanged throughout the culture time, indicating that the cancer cells did not metabolize t-PTER or QUER.

Example 3

Interaction between B16 Melanoma Cells and Endothelial Cells "in vitro"

Isolation and Culture of Hepatic Sinusoidal Endothelium

C57BL/6J mice were used (male, 10 to 12 weeks old) from IFFA Credo (L'Arbreole, France). The hepatic sinusoidal endothelium (HSE) was separated and identified as described previously (20). The sinusoidal cells were separated in a gradient of 17.5% metrizamide (w/v). The HSE cultures were established and maintained in pyrogen-free DMEM supplemented as described previously for the B16M-F10 cells. Differential adhesion of the endothelial cells to the collagen matrix and washing permitted complete removal of other types of sinusoidal cells (Kupffer's cells, astrocytes, lymphocytes) from the culture flasks.

Tests of Adhesion and Cytotoxicity between B16 Melanoma Cells and Endothelial Cells The B16M-F10 cells were labeled with 2',7'-bis-(2-carboxyethyl)-5-(and -6)-carboxyfluorescein acetoxymethyl ester (BCECF-AM; Moleculer Probes, Eugene, Oreg., USA) ($10^6$ cells were incubated for 20 minutes at 37° C. in 1 ml of DMEM buffered with HEPES that contained 50 μg of BCECF-AM and 5 μl of DMSO). After washing, the cells that contained BCECF-AM were resuspended in DMEM buffered with HEPES without phenol red at a concentration of $2.5 \times 10^6$ cells/ml and were added (0.2 ml/well) to the endothelial cell culture (seeded 24 hours previously), as well as to wells of plastic and controls previously treated with collagen. The plates were then incubated at 37° C. and, 20 minutes later, the wells were washed three times with fresh medium, and then their fluorescence was read using a Fluoroskan Ascent FL (Labsystems, Manchester, UK). The number of adhering tumor cells was quantified with arbitrary fluorescence units based on the percentage relative to the initial number of B16M-F10 cells added to the HSE culture (20). The damage caused to the B16M-F10 cells during their adhesion in vitro to the HSE was evaluated as described previously (21) using tumor cells labeled with calcein-AM (Molecular Probes, Eugene, Oreg., USA). The integrity of the B16M-F10 cells cultivated on their own was evaluated by exclusion of trypan blue and measuring the lactate dehydrogenase released to the extracellular medium (22). The other reagents used in the tumoral cytotoxicity experiments were from Sigma.

Cytokines

Recombinant murine TNF- ($2 \times 10^7$ U/mg of protein) and recombinant murine interferon-(IFN-; $10^5$ U/mg of protein) were obtained from Sigma. The concentrated solutions ($5 \times 10^5$ U TNF-/ml and $25 \times 10^4$ U IFN-/ml) were diluted in sterile saline (0.9% NaCl), adjusted to pH 7.0, and stored at 4° C.

Test of "in-vitro" Invasion of the Monolayer of Hepatic Endothelial Cells by B16 Melanoma Cells The test of invasion of the endothelial cell monolayer by B16M-F10 cells was carried out in accordance with the method of Ohigashi et al. (23) with some modifications. The HSE cells were seeded on culture plates with grids coated with gelatin (1%). When the cells attained confluence, the culture medium was replaced with freshly prepared medium. After 2 hours of incubation, the cultures were washed with DMEM and then the B16M-F10 cells were seeded on the HSE cells, maintaining the culture for 5 days. The invasion capacity of the B16M-F10 cells was measured by counting the number of colonies per 1 $cm^2$ formed under the HSE monolayer using a phase-contrast microscope.

Measurement of $H_2O_2$, Nitrite and Nitrate

The test of production of $H_2O_2$ was based on the $H_2O_2$—dependent oxidation of homovanillic acid (3-methoxy-4-hydroxyphenylacetic acid), mediated by radish peroxidase, to give a highly fluorescent dimer (2,2'-dihydroxydiphenyl-5,5'-diacetic acid) (20). For this purpose, the cells were cultivated in the presence of homovanillic acid 100 μM and 1 U of radish peroxidase/ml. A linear relation was obtained between fluorescence (excitation=312 nm and emission=420 nm) and the amount of $H_2O_2$ in the range 0.1-12 nmol per 2 ml of test sample.

The determinations of nitrite and nitrate were performed using the methodology of Braman and Hendrix (24). Briefly, the levels of $NO_2^-$ were determined by chemiluminescence detection of NO in the presence of iodide/acetic acid (which reduces the $NO_2^-$, but not the $NO_3^-$, to NO). Total $NO_x$ ($NO_2^-$ plus $NO_3^-$) was determined by measuring the production of NO in samples submitted to a boiling solution of $VCl_3$/HCl (which will reduce both the $NO_2^-$ and the $NO_3^-$ to NO). The levels of $NO_3^-$ were determined by subtracting the value for $NO_2^-$ from the value for $NO_x$. Quantification was effected using a standard curve obtained from known quantities of $NO_2^-$ and $NO_3^-$.

Flow Cytometry

Expression of the intercellular adhesion molecules was analyzed by flow cytometry (25). For this purpose, B16M-F10 cells ($1 \times 10^6$) were incubated for 1 hour at 4° C. with 1 μg of a monoclonal antibody (rat IgG2b type, clone PS/2 from Serotec, Oxford, UK) against the mouse very late activation antigen 4 (VLA-4). The HSE ($1 \times 10^6$ cells) was incubated with 2 μg of a monoclonal antibody (rat IgG type, kappa, clone M/K-2 from R & D Systems, Minn., USA) against the mouse vascular cellular adhesion molecule 1 (VCAM-1). The B16M-F10 and HSE cells were washed twice with PBS and were then treated, for 1 hour at 4° C., with a goat antibody to rat immunoglobins labeled with fluorescein isothiocyanate (Serotec). After washing twice with PBS, the cells were analyzed using a fluorescence-activated cell separator (FACscan, Becton Dickinson, Sunnyvale, Calif., USA). The proliferation and/or viability of the B16M-F10 and HSE cells were not affected by these monoclonal antibodies (even after adding up to 100 μg of antibody/ml of culture medium) (data not shown).

In addition to the effect of PTER+QUER on tumor growth, we investigated the antimetastatic potential. The interaction of B16M-F10 and HSE cells was studied in vitro first. On the basis of the results obtained previously, we chose brief periods of exposure (60 minutes) of the metastatic cells to the polyphenols (at the concentrations measured in the plasma after their i.v. administration). Since the interaction of the metastatic cells with the endothelial cells and Kupffer's cells activates the local release of proinflammatory cytokines [promoters of adhesion of cancer cells to the endothelium and of invasion (14, 31)], we investigated the effect of the polyphenols on the adhesion of B16M-F10 cells to the HSE in the presence of TNF- and IFN-—this combination of cytokines induces maximum activation of the HSE (see ref. 20 and the references therein) (Table 3). As described previously, t-RESV inhibits the adhesion of tumor cells to the endothelium (~47%) without increasing the HSE-induced cytotoxicity on the metastatic cells (14). A similar effect (~60% inhibition of adhesion) was found in the presence of t-PTER (Table 3). In contrast, QUER increased the death of B16M-F10 cells induced by the HSE (~48%) but without affecting the level of adhesion (Table 3). As shown in Table 3, by combining t-PTER+QUER we obtained the lowest percentage adhesion of B16M-F10 cells to the HSE and the highest percentage cytotoxicity in the adhering cancer cells. On testing the invasion in vitro of monolayers of hepatic endothelial cells by B16M-F10 cells, we found a marked decrease (~74%) in the number of colonies formed in the presence of t-PTER and QUER (Table 3).

TABLE 3

Effect of brief exposure to resveratrol, pterostilbene and/or quercetin on the interaction in vitro between B16M-F10 cells and the vascular endothelium.

| Additions | Tumor cells | | Number of colonies penetrated per cm$^2$ |
|---|---|---|---|
| | Adhesion (%) | Cytotoxicity (% of adhering) | |
| None | 100 ± 15 | 15 ± 2 | 157 ± 17 |
| RESV | 53 ± 7** | 12 ± 3 | 104 ± 12** |
| PTER | 40 ± 6** | 19 ± 3* | 89 ± 9** |
| QUER | 98 ± 11 | 52 ± 6** | 106 ± 15** |
| RESV + PTER | 32 ± 4** | 17 ± 4 | 77 ± 8** |
| RESV + QUER | 55 ± 7** | 55 ± 7** | 70 ± 7** |
| PTER + QUER | 37 ± 5** | 54 ± 5** | 41 ± 5** |

HSE cells, previously cultured for 24 hours [±polyphenol(s), added 12 hours from seeding and removed by washing 60 minutes later], were cocultured with B16M-F10 cells previously cultured for 72 hours [±polyphenol(s), as in FIG. 2]. Cytokines [100 units of TNF-/ml and 50 units of IFN-/ml, see (20)] or the vehicle (physiological saline) were added to the culture media 12 hours before starting the cocultures. The proportion of adhesion of the tumor cells to the HSE was ~1:1 in the cultures treated with cytokines in the absence of polyphenols (this value was assigned an adhesion level of 100%). In the experiments of adhesion between B16M-F10 cells and endothelial cells, 20 minutes after adding the B16M-F10 to the HSE, the plates were washed in the manner described in the methodology. In the tests of endothelium-induced cytotoxicity on the B16M-F10 cells, the tumor damage (expressed as the percentage of tumor cells that lost viability during the incubation period of 4-6 hours, see the methodology) was determined after 6 hours of incubation. During the 6-hour incubation period, the percentage viability of the HSE cells was 99-100% in all cases. All of the tests were carried out in the absence or in the presence of t-RESV (12 μM), t-PTER (40 μM), and/or QUER (20 μM). The values represent mean values±SD from 5-6 different experiments in each case. *P<0.05, **p<0.01 comparing the incubations in the presence and in the absence of polyphenol(s).

The adhesion of B16M-F10 cells to the HSE induces the release of NO and $H_2O_2$ from the endothelium, causing partial death of the metastatic cells (20). We had previously observed that $H_2O_2$ was not cytotoxic in the absence of NO, however, the NO-induced tumoral cytotoxicity was increased by $H_2O_2$ owing to the formation of potent oxidants such as $^-H$ and $^-ONOO$ radicals by a process that is dependent on metal ions (20). During the interaction of B16M-F10 and HSE in the presence of t-PTER and QUER (both present×60 minutes as in Table 3), the $NO_x$ that had accumulated in the culture medium during a period of 3 hours was not significantly different from that of the controls (7.5±1.3 nmol/10$^6$ cells; n=6). In contrast, t-PTER and QUER lowered the production of $H_2O_2$ from 70±12 nmol/10$^6$ cells (controls) to 34±10 nmol/10$^6$ cells (n=5-6 in both cases, P>0.01). It is inferred from this that the antioxidizing potential of these polyphenols should contribute, at least partially, to checking the cytotoxicity induced by the HSE on the B16M-F10 cells. Although, obviously, other mechanisms activated by t-PTER and/or QUER are promoting the decrease in metastatic activity (Table 3). In this sense, since $H_2O_2$ can act as a growth-promoting intracellular messenger (32), at least partially, the inhibition of tumor growth induced by t-PTER and QUER (FIG. 2) might be explained by a decrease of $H_2O_2$—dependent intracellular signals.

Example 4

Growth of Metastases in the Liver RT-PCR and Detection of mRNA Expression

Total RNA was isolated with Trizol (Invitrogen, San Diego, Calif., USA). The cDNA was obtained using a hexamer and the MultiScribe inverse transcriptase kit, following the manufacturer's instructions (TaqMan RT Reagents, Applied Biosystems, Foster City, Calif., USA). Quantitative PCR was carried out using AmpliTaq Gold DNA polymerase (Applied Biosystems) with specific primers: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16.

Quantification of the transcription of each mRNA was carried out with SYBR Green I and an iCycler detection system (Biorad, Hercules, Calif., USA), relating it to the mRNA of glyceraldehyde-3P-dehydrogenase (GAPDH). The target cDNAs were amplified in separate tubes using the following conditions: 10 minutes at 95° C., 40 cycles of amplification (denaturing at 95° C. for 30 seconds; pairing and extension at 60° C. for 1 minute per cycle). The increase in fluorescence was measured in real time during the extension stage. The threshold cycle ($C_T$) was determined, and then the expression relative to the gene was calculated as: change of expression=$2^{-(C_T)}$, where $C_T$=$C_T$ target–$C_T$ GAPCH, and ($C_T$)=$C_T$treated–$C_T$control.

Transfer and Analysis of the bcl-2 Gene

The Tet-off gene expression system (Clontech, Palo Alto, Calif., USA) was used for inserting the mouse bcl-2 gene and transfecting the B16M-F10 cells, as described previously (26) and following the manufacturer's instructions. The protein Bcl-2 was quantified in the soluble cytosolic fraction by enzyme immunoassay (27) using a test based on a monoclonal antibody from Sigma (San Luis, Mo., USA) (a Bcl-2 unit was defined as the amount of Bcl-2 protein in 1000 non-transfected B16M-F10 cells).

Experimental Metastases

Hepatic metastases were induced by i.v. inoculations (portal vein), in anesthetized mice (Nembutal, 50 mg/kg i.p.), of 4×10$^5$ viable B16M-F10 cells suspended in 0.2 ml of DMEM. The mice were sacrificed by cervical dislocation 10 days after inoculation. The livers were fixed by immersion for 24 hours at 22° C. in 10% formaldehyde in PBS (pH 7.4), and were subsequently embedded in paraffin. The density of metastases (average number of foci/100 mm$^3$ of liver detected in fifteen sections of 10×10 mm$^2$ per liver) and the volume of metastases (average percentage of liver volume occupied by metastases) were determined as described previously (22).

Presentation of the Results and Statistical Significance

The data are presented as mean value±SD corresponding to the stated number of different experiments. Statistical analyses were carried out using the Student t-test, and values of P<0.05 were regarded as significant.

This methodology makes it possible for the effect of PTER and QUER to be studied in vivo. For this purpose, mice were inoculated with B16M-F10 control cells or B16M-F10/Tet-Bcl-2 which overexpressed Bcl-2. Both subgroups of cells were cultivated beforehand in the absence or in the presence of t-PTER and QUER. B16M-F10 cells were cultivated for 72 hours. t-RESV (12 µM), t-PTER (40 µM), and QUER (20 µM) were added at 6, 30 and 54 hours of culture time, and were present in each case for just 60 minutes. Then they were removed from the culture flasks by washing (3 times with PBS) and the medium was renewed. The levels of Bcl-2 in the B16M-F10 control cells and cells treated with Tet-Bcl-2 were 24±5 and 105±14 units/mg of protein, respectively (n=5 in each case, P<0.01). The number of adhering cells shown in the table was calculated at 60 minutes postinjection (no significant differences were found when the measurements were effected at 30, 120, 180, 240 or 360 minutes postinjection, data not shown). The number of intact cells was calculated at 6 hours postinjection. The experimental microscopy data in vivo are mean values±SD corresponding to 4-5 different experiments. The growth of metastases in the liver was evaluated as stated in the corresponding section of the description, and in this case the mice were treated daily (×10 days) with t-PTER and/or QUER (20 mg/kg of body weight) administered i.v. (the data are mean values±SD corresponding to 25 mice per group). A similar method and equal number of mice per group were used for evaluating the survival of the carrier animals. The test of significance relates, in all the groups, to comparison between cases with PTER and/or QUER and cases without additions (*P<0.05 and **P<0.01), and to comparison between the B16M-F10/Tet-Bcl-2 cells with the B16M-F10 control cells (+P<0.05, ++P<0.01). As shown in Table 4, t-PTER and QUER lowered the intracellular levels of Bcl-2 and the number of B16M-F10 and B16M-F10/Tet-Bcl-2 cells adhering to the endothelium. However, owing to differences in the level of Bcl-2 between the two cellular subgroups, t-PTER and QUER only lowered the percentage of adhering and intact cells in the case of the B16M-F10 control cells (Table 4). In consequence, although the untreated mice, which had been inoculated with B16M-F10 or B16M-F10/Tet-Bcl-2 cells, displayed similar levels of metastatic growth in the liver and a similar survival of the host, the effect of daily i.v. administration of t-PTER and QUER was more evident in the B16M-F10 control cells: 74% decrease in the density and volume of metastases and a doubling of the survival of the carrier host (Table 4). This is the first time that the combined administration in vivo of natural polyphenols has induced inhibition of metastatic growth of a highly malignant tumor and an increase in the survival of the carrier. As can be seen in the aforementioned Table 4, PTER and QUER, separately, also lower the density and volume of the metastases, but their combination produces a synergistic effect on the tumor greater than 100% if we take as the baseline the respective action of each one separately. Conversely, separately, neither of these compounds significantly increased the survival of the host cells, compared with the doubling of the survival rate observed with the combined action of both polyphenols.

TABLE 4

Growth of metastases in the liver of mice after intrasplenic injection of B16M-F10 cells treated with PTER and QUER and which contained different levels of Bcl-2.

| | | Melanoma | |
| --- | --- | --- | --- |
| | Additions | B16M-F10 | B16M-F10/ter-Bcl-2 |
| Intracellular levels of Bcl-2 before inoculation (units/mg protein) | NONE | 35 ± 5 | 160 ± 25++ |
| | PTER | 21 ± 4** | 151 ± 18++ |
| | QUER | 9 ± 3** | 125 ± 13*++ |
| | PTER + QUER | 7 ± 2** | 118 ± 16**++ |
| Number of cells adhering to the HSE (average number per lobe) | NONE | 45 ± 7 | 42 ± 6 |
| | PTER | 20 ± 5** | 21 ± 4** |
| | QUER | 46 ± 9 | 40 ± 7 |
| | PTER + QUER | 18 ± 4** | 17 ± 3** |
| Intact cells (percentage of cells adhering to the HSE) | NONE | 83 ± 14 | 85 ± 13 |
| | PTER | 85 ± 17 | 91 ± 20 |
| | QUER | 52 ± 8** | 87 ± 13++ |
| | PTER + QUER | 48 ± 10** | 90 ± 17++ |
| Density of metastases (number of foci/100 mm$^3$) | NONE | 27 ± 5 | 29 ± 5 |
| | PTER | 18 ± 4** | 15 ± 3** |
| | QUER | 15 ± 4** | 26 ± 516++ |
| | PTER + QUER | 7 ± 2** | 20 ± 4*++ |
| Volume of metastases (percentage of liver volume) | NONE | 22 ± 4 | 25 ± 6 |
| | PTER | 14 ± 4** | 15 ± 3** |
| | QUER | 12 ± 3** | 24 ± 5++ |
| | PTER + QUER | 6 ± 2** | 19 ± 5++ |
| Survival of the carrier (days) | NONE | 13 ± 2 | 12 ± 1 |
| | PTER | 15 ± 2 | 12 ± 2 |
| | QUER | 15 ± 1 | 13 ± 2 |
| | PTER + QUER | 27 ± 3** | 14 ± 2** |

SEQUENCE LISTING

<160> NUMBER OF SEQ ID NOS: 16

Figure 1:
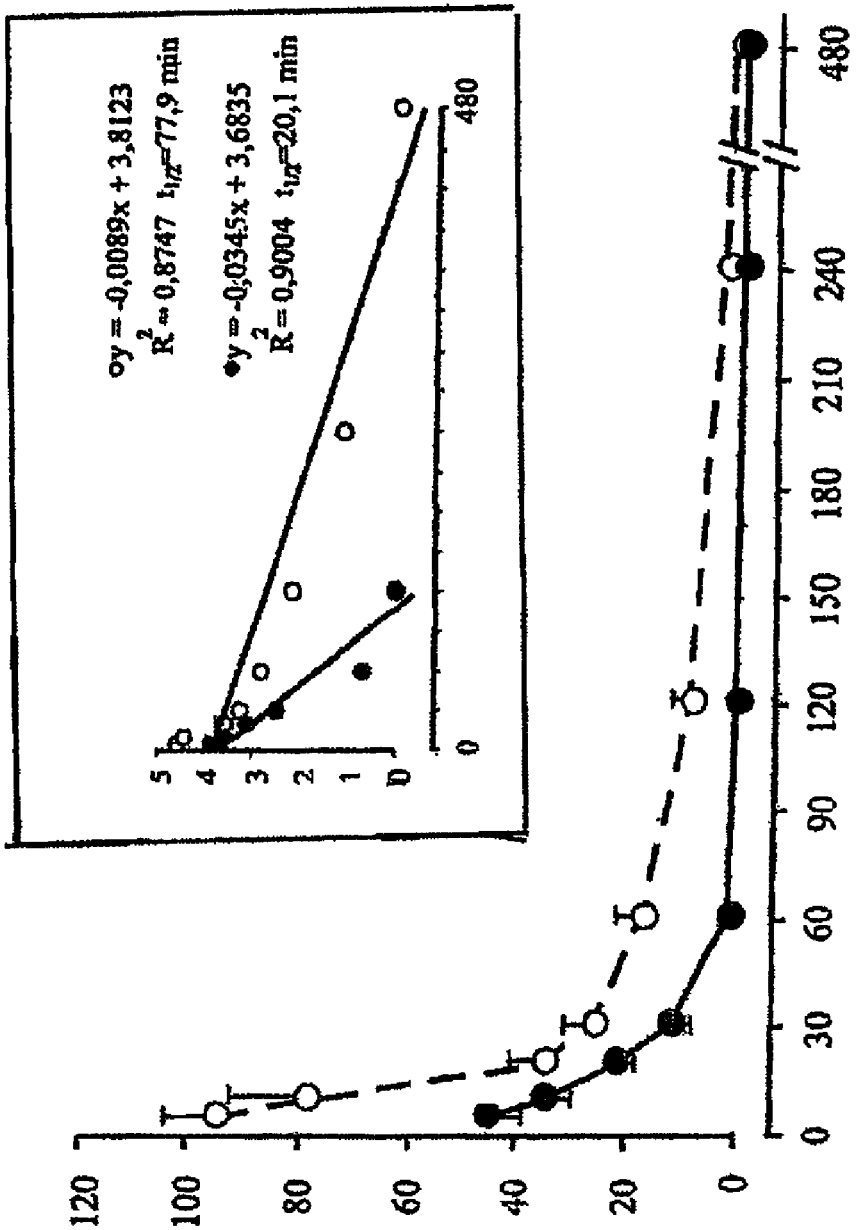
FIG. 1. Plasma levels and half-life of pterostilbene and quercetin after intravenous administration in mice. The animals were treated with t-PTER (empty circles) or QUER (filled circles) (20 mg/kg of body weight). The plasma levels were determined as explained in the description. The results are mean values±SD corresponding to 5-6 mice at each time point, measured in minutes (abscissa). In the box, the same is shown on a logarithmic scale.
Figure 2:
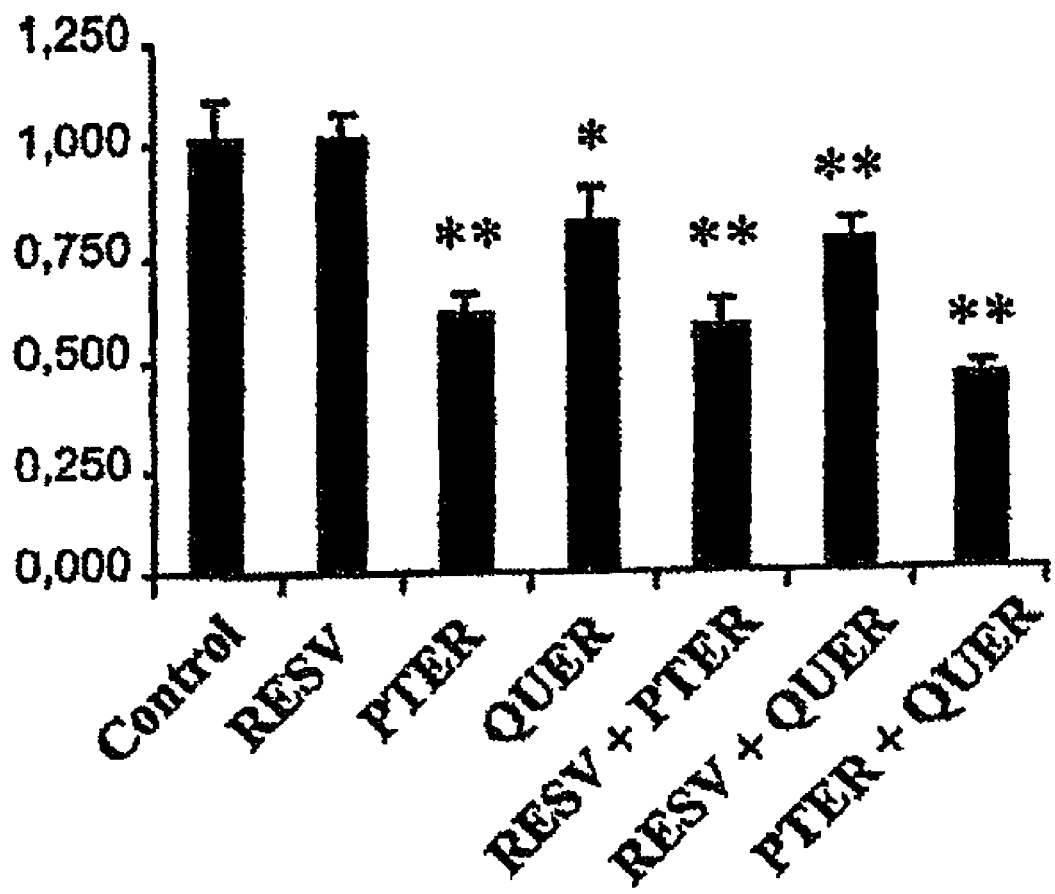
FIG. 2. Inhibition in vitro of the growth of B16M-F10 cells by brief exposure to resveratrol (RESV), pterostilbene (PTER) and/or quercetin (QUER). All the points are mean values±SD corresponding to 5-6 independent experiments. *P<0.05, **P<0.01 compared with the control values.

<210> SEQ ID NO 1
<211> LENGTH: 23
<212> TYPE: DNA

```
<213> ORGANISM: Artificial Sequence
<220> FEATURE:
<223> OTHER INFORMATION: Primer BAX 5'-3'

<400> SEQUENCE: 1
aagctgagcg agtgtctccg gcg                                          23

<210> SEQ ID NO 2
<211> LENGTH: 25
<212> TYPE: DNA
<213> ORGANISM: Artificial Sequence
<220> FEATURE:
<223> OTHER INFORMATION: Primer BAX 3'-5'

<400> SEQUENCE: 2
gccacaaaga tggtcactgt ctgcc                                        25

<210> SEQ ID NO 3
<211> LENGTH: 24
<212> TYPE: DNA
<213> ORGANISM: Artificial Sequence
<220> FEATURE:
<223> OTHER INFORMATION: Primer BAK 5'-3'

<400> SEQUENCE: 3
agtgagggca gaggtgagag ttca                                         24

<210> SEQ ID NO 4
<211> LENGTH: 25
<212> TYPE: DNA
<213> ORGANISM: Artificial Sequence
<220> FEATURE:
<223> OTHER INFORMATION: Primer BAK 3'-5'

<400> SEQUENCE: 4
cacagttgct tctgctggag tagtt                                        25

<210> SEQ ID NO 5
<211> LENGTH: 25
<212> TYPE: DNA
<213> ORGANISM: Artificial Sequence
<220> FEATURE:
<223> OTHER INFORMATION: Primer BAD 5'-3'

<400> SEQUENCE: 5
ccagtgatct tctgctccac atccc                                        25

<210> SEQ ID NO 6
<211> LENGTH: 24
<212> TYPE: DNA
<213> ORGANISM: Artificial Sequence
<220> FEATURE:
<223> OTHER INFORMATION: Primer BAD 3'-5'

<400> SEQUENCE: 6
caacttagca caggcacccg aggg                                         24

<210> SEQ ID NO 7
<211> LENGTH: 25
<212> TYPE: DNA
<213> ORGANISM: Artificial Sequence
<220> FEATURE:
<223> OTHER INFORMATION: Primer BID 5'-3'

<400> SEQUENCE: 7
acaaggccat gctgataatg acaat                                        25
```

<210> SEQ ID NO 8
<211> LENGTH: 24
<212> TYPE: DNA
<213> ORGANISM: Artificial Sequence
<220> FEATURE:
<223> OTHER INFORMATION: Primer BID 3'-5'

<400> SEQUENCE: 8
cagatacact caagctgaac gcag                                              24

<210> SEQ ID NO 9
<211> LENGTH: 24
<212> TYPE: DNA
<213> ORGANISM: Artificial Sequence
<220> FEATURE:
<223> OTHER INFORMATION: Primer Bcl-2 5'-3'

<400> SEQUENCE: 9
ctcgtcgcta ccgtcgtgac ttcg                                              24

<210> SEQ ID NO 10
<211> LENGTH: 25
<212> TYPE: DNA
<213> ORGANISM: Artificial Sequence
<220> FEATURE:
<223> OTHER INFORMATION: Primer Bcl-2 3'-5'

<400> SEQUENCE: 10
cagatgccgg ttcaggtact cagtc                                             25

<210> SEQ ID NO 11
<211> LENGTH: 23
<212> TYPE: DNA
<213> ORGANISM: Artificial Sequence
<220> FEATURE:
<223> OTHER INFORMATION: Primer Bcl-w 5'-3'

<400> SEQUENCE: 11
cgagtttgag acccgtttcc gcc                                               23

<210> SEQ ID NO 12
<211> LENGTH: 23
<212> TYPE: DNA
<213> ORGANISM: Artificial Sequence
<220> FEATURE:
<223> OTHER INFORMATION: Primer Bcl-w 3'-5'

<400> SEQUENCE: 12
gcacttgtgc caccaaaggc tcc                                               23

<210> SEQ ID NO 13
<211> LENGTH: 24
<212> TYPE: DNA
<213> ORGANISM: Artificial Sequence
<220> FEATURE:
<223> OTHER INFORMATION: Primer Bcl-xL 5'-3'

<400> SEQUENCE: 13
tggagtaaac tgggggtcgc atcg                                              24

<210> SEQ ID NO 14
<211> LENGTH: 22
<212> TYPE: DNA
<213> ORGANISM: Artificial Sequence
<220> FEATURE:
<223> OTHER INFORMATION: Primer Bcl-xL 3'-5'

```
<400> SEQUENCE: 14
agccaccgtc atgcccgtca gg                                          22

<210> SEQ ID NO 15
<211> LENGTH: 23
<212> TYPE: DNA
<213> ORGANISM: Artificial Sequence
<220> FEATURE:
<223> OTHER INFORMATION: Primer Glyceraldehyde-3P-dehydrogenase 5'-3'

<400> SEQUENCE: 15
cctggagaaa cctgccaagt atg                                         23

<210> SEQ ID NO 16
<211> LENGTH: 23
<212> TYPE: DNA
<213> ORGANISM: Artificial Sequence
<220> FEATURE:
<223> OTHER INFORMATION: Primer Glyceraldehyde-3P-dehydrogenase 3'-5'

<400> SEQUENCE: 16
ggtcctcagt gtagcccaag atg                                         23
```

The invention claimed is:

1. A method of treating cancer in a subject which comprises intravenously administering to a subject in need thereof a therapeutically effective amount of a combination of pterostilbene and quercetin (PTER+QUER), including the pharmaceutically acceptable salts thereof.

2. The method as claimed in claim 1, characterized in that PTER and QUER are administered in combination with a pharmaceutically acceptable excipient.

3. The method as claimed in claim 1 characterized in that the treatment is treatment of a hepatic carcinoma.

* * * * *